(12) United States Patent
Nakajima et al.

(10) Patent No.: US 10,549,905 B2
(45) Date of Patent: Feb. 4, 2020

(54) AEROSOL PRODUCT FOR FORMING GEL COMPOSITION

(71) Applicant: Toyo Aerosol Industry Co., Ltd., Tokyo (JP)

(72) Inventors: Yasutomo Nakajima, Tokyo (JP); Makoto Tsubouchi, Tokyo (JP); Hokuto Kamijyo, Tokyo (JP); Tomoyuki Niinomi, Tokyo (JP); Remi Ikeda, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/556,380

(22) PCT Filed: Mar. 9, 2016

(86) PCT No.: PCT/JP2016/057301
§ 371 (c)(1),
(2) Date: Sep. 7, 2017

(87) PCT Pub. No.: WO2016/147972
PCT Pub. Date: Sep. 22, 2016

(65) Prior Publication Data
US 2018/0044099 A1 Feb. 15, 2018

(30) Foreign Application Priority Data
Mar. 13, 2015 (JP) .................................. 2015-050130

(51) Int. Cl.
*A61K 8/73* (2006.01)
*B65D 83/62* (2006.01)
(Continued)

(52) U.S. Cl.
CPC ............. *B65D 83/62* (2013.01); *A45D 34/02* (2013.01); *A45D 34/04* (2013.01); *A61K 6/10* (2013.01);
(Continued)

(58) Field of Classification Search
CPC . A61K 8/02; A61K 8/046; A61K 8/31; A61K 8/34; A61K 8/345; A61K 8/362; A61K 8/891
See application file for complete search history.

(56) References Cited

U.S. PATENT DOCUMENTS 4,948,575 A 8/1990 Cole et al.
2003/0044432 A1 3/2003 Manetta et al.
(Continued)

FOREIGN PATENT DOCUMENTS

EP 1386613 A1 * 2/2004 ........... A61K 8/0204
EP 2116233 A1 11/2009
(Continued)

OTHER PUBLICATIONS

International Search Report dated Apr. 5, 2016 for PCT/JP2016/057301.
(Continued)

*Primary Examiner* — Micah Paul Young
(74) *Attorney, Agent, or Firm* — Lucas & Mercanti, LLP

(57) ABSTRACT

The present invention has as its object the provision of an aerosol product for forming a gel composition. The aerosol product has high storage stability and can form a desired gel composition easily and stably.
The aerosol product for forming a gel composition of the present invention has a double-structure container including a propellant filling space and two liquid concentrate filling spaces and having a discharging mechanism for simultaneously discharging the contents filled in the two liquid
(Continued)

concentrate filling spaces. The propellant filling space is filled with a propellant composed of a compressed gas, a first liquid concentrate filling space is filled with a first liquid concentrate composition containing water and a water-soluble alginic acid salt, and a second liquid concentrate filling space contains a second liquid concentrate composition containing water and a dissociative calcium salt. The first liquid concentrate composition and the second liquid concentrate composition are mixed to form a gel composition.

10 Claims, 2 Drawing Sheets

(51) Int. Cl.
| | | |
|---|---|---|
| | *A61Q 19/00* | (2006.01) |
| | *A61K 8/19* | (2006.01) |
| | *B65D 83/68* | (2006.01) |
| | *A61K 8/04* | (2006.01) |
| | *C11D 17/00* | (2006.01) |
| | *A45D 34/02* | (2006.01) |
| | *A61K 6/10* | (2006.01) |
| | *C11D 3/22* | (2006.01) |
| | *C11D 7/10* | (2006.01) |
| | *C11D 3/04* | (2006.01) |
| | *A61K 8/02* | (2006.01) |
| | *A45D 34/04* | (2006.01) |

(52) U.S. Cl.
CPC ............ *A61K 8/0212* (2013.01); *A61K 8/042* (2013.01); *A61K 8/046* (2013.01); *A61K 8/19* (2013.01); *A61K 8/733* (2013.01); *A61Q 19/00* (2013.01); *B65D 83/68* (2013.01); *B65D 83/682* (2013.01); *C11D 3/046* (2013.01); *C11D 3/222* (2013.01); *C11D 7/10* (2013.01); *C11D 17/003* (2013.01); *C11D 17/0043* (2013.01); *A45D 2200/057* (2013.01); *A45D 2200/058* (2013.01); *A61K 2800/87* (2013.01); *A61K 2800/88* (2013.01); *A61K 2800/882* (2013.01)

(56) References Cited

U.S. PATENT DOCUMENTS

| | | |
|---|---|---|
| 2003/0108487 A1 | 6/2003 | Bara |
| 2004/0219230 A1 | 11/2004 | Tanaka |
| 2005/0205086 A1 | 9/2005 | Tamarkin et al. |
| 2006/0054634 A1* | 3/2006 | Mekata ............... B05B 11/3081 222/94 |
| 2014/0246515 A1 | 9/2014 | Nakajima |

FOREIGN PATENT DOCUMENTS

| | | | | |
|---|---|---|---|---|
| GB | 1122796 A | | 8/1968 | |
| JP | H06199638 B1 | | 7/1994 | |
| JP | H11302124 A | | 11/1999 | |
| JP | 2000247831 A | | 9/2000 | |
| JP | 2002128636 A | | 5/2002 | |
| JP | 2004161292 A | * | 6/2004 | ............ B65D 83/62 |
| JP | 2004161292 A | | 6/2004 | |
| JP | 2006137714 A | | 6/2006 | |
| JP | 2009-091365 A | | 4/2009 | |
| KR | 10-2014-0082776 A | | 7/2014 | |

OTHER PUBLICATIONS

Extended European Search Report dated Dec. 6, 2017 from the corresponding European Application No. 16764802.1 and English translation.

Notification of Reason for Refusal dated Oct. 29, 2018 from the corresponding Korean Application No. 10-2017-7028215 and English translation.

* cited by examiner

AEROSOL PRODUCT FOR FORMING GEL COMPOSITION

CROSS REFERENCE TO RELATED APPLICATION

This Application is a 371 of PCT/JP2016/057301 filed on Mar. 9, 2016 which, in turn, claimed the priority of Japanese Patent Application No. 2015-050130 filed Mar. 13, 2015, both applications are incorporated herein by reference.

TECHNICAL FIELD

The present invention relates to an aerosol product for forming a gel composition.

BACKGROUND ART

In the related art, gel compositions having high elasticity have widely been used in daily necessaries, food, and products for the human body such as facial masks and medicinal patches.

Some of widely known methods for producing such gel compositions having high elasticity include a technique for bringing a sodium alginate aqueous solution and a calcium chloride aqueous solution into contact with each other (for example, Patent Literature 1 to Patent Literature 4). In this technique, the ion crosslinking reaction occurs upon contact between the sodium alginate aqueous solution and the calcium chloride aqueous solution to form a gel composition.

However, formation of such a gel composition from two aqueous solutions requires preparation of these aqueous solutions, and formation of a gel composition having stable physical properties requires control of the conditions in which two aqueous solutions are mixed, specifically, for example, the concentration and the mixing ratio of two aqueous solutions. In addition, there is a problem in that it is difficult to stably store sodium alginate and calcium chloride for a long period of time.

CITATION LIST

Patent Literature

Patent Literature 1: Japanese Patent Application Laid-Open No. Hei. 11-302124
Patent Literature 2: Japanese Patent Application Laid-Open No. 2000-247831
Patent Literature 3: Japanese Patent Application Laid-Open No. 2002-128636
Patent Literature 4: Japanese Patent Application Laid-Open No. 2006-137714

SUMMARY OF INVENTION

Technical Problem

The present invention has been made in view of the foregoing circumstances and has as its object the provision of an aerosol product of an aerosol dispenser for forming a gel composition. The aerosol product has high storage stability and can form a desired gel composition easily and stably.

Solution to Problem

An aerosol product for forming a gel composition of the present invention has a double-structure container including a propellant filling space and two independent liquid concentrate filling spaces and having a discharging mechanism for simultaneously discharging contents filled in the two liquid concentrate filling spaces, the propellant filling space in the double-structure container is filled with a propellant composed of a compressed gas, a first liquid concentrate filling space in the double-structure container is filled with a first liquid concentrate composition, and a second liquid concentrate filling space in the double-structure container is filled with a second liquid concentrate composition, the first liquid concentrate composition contains water and a water-soluble alginic acid salt, the second liquid concentrate composition contains water and a dissociative calcium salt, and the first liquid concentrate composition discharged from the first liquid concentrate filling space and the second liquid concentrate composition discharged from the second liquid concentrate filling space are mixed to form a gel composition.

In the aerosol product for forming a gel composition of the present invention, the mixing ratio of the first liquid concentrate composition to the second liquid concentrate composition (the mass of the first liquid concentrate composition: the mass of the second liquid concentrate composition) discharged from the discharging mechanism may preferably be from 0.8:1.2 to 1.2:0.8.

In the aerosol product for forming a gel composition of the present invention, the first liquid concentrate composition may preferably have a viscosity of 10 to 125,000 mPa·s at a temperature of 20° C., and the second liquid concentrate composition may preferably have a viscosity of 10 to 125,000 mPa·s at a temperature of 20° C.

In the aerosol product for forming a gel composition of the present invention, the water-soluble alginic acid salt contained in the first liquid concentrate composition may preferably be at least one selected from the group consisting of sodium alginate, potassium alginate, and ammonium alginate.

Advantageous Effects of Invention

The aerosol product for forming a gel composition of the present invention has a double-structure container having a discharging mechanism for simultaneously discharging the contents filled in two liquid concentrate filling spaces. One of the two liquid concentrate filling spaces is filled with a first liquid concentrate composition containing water and a water-soluble alginic acid salt. The other is filled with a second liquid concentrate composition containing water and a dissociative calcium salt.

Therefore, the first liquid concentrate composition and the second liquid concentrate composition are mixed to form a gel composition through the ion crosslinking reaction. Since the first liquid concentrate composition and the second liquid concentrate composition can be simultaneously discharged in suitable amounts from the liquid concentrate filling spaces in the double-structure container, respectively, the first liquid concentrate composition and the second liquid concentrate composition can always be mixed in a constant quantitative ratio. As a result, there is no possibility that the amount of one liquid concentrate composition discharged is much larger than the amount of another liquid concentrate composition discharged.

Moreover, the long-term storage stability can be obtained because neither the first liquid concentrate composition nor the second liquid concentrate composition is exposed to the air outside the container.

Therefore, the aerosol product for forming a gel composition of the present invention has high storage stability and can form a desired gel composition easily and stably.

DESCRIPTION OF EMBODIMENTS

Figure 1:
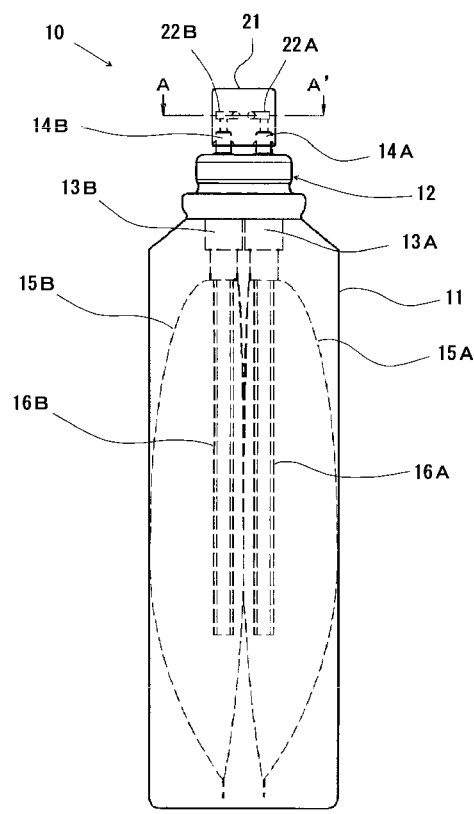
FIG. 1 is an explanatory view illustrating an example structure of a double-structure container used for an aerosol product for forming a gel composition of the present invention.

An aerosol product for forming a gel composition of the present invention has a double-structure container including a propellant filling space and two independent liquid concentrate filling spaces and having a discharging mechanism for simultaneously discharging the contents filled in these two liquid concentrate filling spaces. In this double-structure container, the propellant filling space is filled with a propellant composed of a compressed gas. A first liquid concentrate filling space is filled with a first liquid concentrate composition containing water and a water-soluble alginic acid salt, and a second liquid concentrate filling space is filled with a second liquid concentrate composition containing water and a dissociative calcium salt.

In the aerosol product for forming a gel composition of the present invention, the first liquid concentrate composition and the second liquid concentrate composition discharged simultaneously from the first liquid concentrate filling space and the second liquid concentrate filling space, respectively, are mixed to cause an ion crosslinking reaction, so that an alginate aqueous solution containing water and the water-soluble alginic acid salt is gelled by the dissociative calcium salt (specifically, calcium ions) to form a gel composition.

First Liquid Concentrate Composition:

The first liquid concentrate composition is a liquid containing a water-soluble alginic acid salt dissolved in a liquid medium containing water. In other words, the first liquid concentrate composition is composed of an alginate aqueous solution.

The water-soluble alginic acid salt, which is an essential component of the first liquid concentrate composition, may preferably be at least one selected from the group consisting of sodium alginate, potassium alginate, and ammonium alginate.

The content ratio of the water-soluble alginic acid salt may preferably be 0.5% to 25% by mass per 100% by mass of the first liquid concentrate composition.

If the content ratio of the water-soluble alginic acid salt is too high, the water-soluble alginic acid salt may not be dissolved well in the first liquid concentrate composition.

If the content ratio of the water-soluble alginic acid salt is too low, sufficient gel formability may not be obtained.

Water, which is an essential component of the first liquid concentrate composition, is a main component of the liquid medium.

Specific examples of water used in the first liquid concentrate composition include purified water and ion-exchanged water.

The content ratio of water may preferably be 75% to 99.5% by mass per 100% by mass of the first liquid concentrate composition in consideration of, for example, the relationship with the content ratio of other components.

The first liquid concentrate composition may contain optional components as desired, in addition to the essential components (specifically, water and the water-soluble alginic acid salt).

Examples of the optional components include a preservative, a pH adjuster, a chelating agent, a thickener, a coloring agent, a flavor, and components (for example, active ingredients) required depending on the intended use of the aerosol product for forming a gel composition.

The first liquid concentrate composition constituted by the essential components and the optional components as described above may preferably have a viscosity of 10 to 125,000 mPa·s at a temperature of 20° C.

If the viscosity of the first liquid concentrate composition is too high, it is difficult to discharge the first liquid concentrate composition. In addition, the first liquid concentrate composition may not be discharged in a desired amount associated with the amount of the second liquid concentrate composition discharged.

If the viscosity of the first liquid concentrate composition is too low, the first liquid concentrate composition may not be discharged in a desired amount associated with the amount of the second liquid concentrate composition discharged.

Second Liquid Concentrate Composition:

The second liquid concentrate composition is a liquid containing a dissociative calcium salt in a liquid medium containing water.

In this second liquid concentrate composition, the dissociative calcium salt may be dissolved in the liquid medium, or the dissociative calcium salt may partially or entirely be dispersed in the liquid medium.

The dissociative calcium salt, which is an essential component of the second liquid concentrate composition, dissolves and dissociates to release calcium ions ($Ca^{2+}$).

Specifically, the dissociative calcium salt contained in the second liquid concentrate composition is to be dissolved in a mixture of the first liquid concentrate composition and the second liquid concentrate composition so that the dissociative calcium salt dissociates to release calcium ions. The dissociative calcium salt includes a dissociative calcium salt that releases calcium ions when it is dissolved in the second liquid concentrate composition, and a dissociative calcium salt that releases calcium ions when it is dissolved in a mixture of the second liquid concentrate composition and the first liquid concentrate composition though it is partially or entirely dispersed and undissolved in the second liquid concentrate composition. In a mixture of the first liquid concentrate composition and the second liquid concentrate composition in which the dissociative calcium salt is partially or entirely dispersed, the ion crosslinking reaction occurs and the dissociation reaction of the dissociative calcium salt occurs through, for example, the shift of chemical equilibrium and the actions of a chelating agent and a pH adjuster, which are added as desired, to release calcium ions.

The dissociative calcium salt contained in the second liquid concentrate composition may be either an inorganic calcium salt or an organic calcium salt. Specific examples of the calcium salts include easily soluble calcium salts, such as calcium chloride and calcium lactate, slightly soluble calcium salts, such as calcium sulfate and calcium citrate, and insoluble calcium salts, such as calcium carbonate and dibasic calcium phosphate. These may be used either singly or in any combination thereof.

The content ratio of the dissociative calcium salt may preferably be 0.3% to 20% by mass per 100% by mass of the second liquid concentrate composition.

If the content ratio of the dissociative calcium salt is too high or too low, sufficient gel formability may not be obtained in either case.

Water, which is an essential component of the second liquid concentrate composition, is a main component of the liquid medium.

Specific examples of water used in the second liquid concentrate composition include purified water and ion-exchanged water.

The content ratio of water may preferably be 80% to 99.7% by mass per 100% by mass of the second liquid concentrate composition in consideration of, for example, the relationship with the content ratios of other components.

The second liquid concentrate composition may contain optional components as desired, in addition to the essential components (specifically, water and the dissociative calcium salt).

Examples of the optional components include a preservative, a viscosity modifier, a pH adjuster, and components (for example, active ingredients) required depending on, for example, the type of dissociative calcium salt and the intended use of the aerosol product for forming a gel composition.

The second liquid concentrate composition constituted by the essential components and the optional components as described above may preferably have a viscosity of 10 to 125,000 mPa·s at a temperature of 20° C.

If the viscosity of the second liquid concentrate composition is too high, it is difficult to discharge the second liquid concentrate composition. In addition, the second liquid concentrate composition may not be discharged in a desired amount associated with the amount of the first liquid concentrate composition discharged.

If the viscosity of the second liquid concentrate composition is too low, the second liquid concentrate composition may not be discharged in a desired amount associated with the amount of the first liquid concentrate composition discharged.

Propellant:

A compressed gas is used as a propellant.

Examples of the compressed gas include nitrous oxide gas, nitrogen gas, carbon dioxide gas and a mixture of these gases.

This propellant is not discharged from the propellant filling space into the outside of the double-structure container along with simultaneous discharge of the first liquid concentrate composition and the second liquid concentrate composition.

The propellant may preferably be enclosed such that the pressure applied when the double-structure container is filled with the propellant is 0.3 to 1.2 MPa at 25° C.

If the pressure applied when the double-structure container is filled with the propellant (product inner pressure) is too high or too low, in both cases, the contents may not be sprayed in favorable conditions.

Double-Structure Container:

The double-structure container of the aerosol product for forming a gel composition of the present invention includes a propellant filling space to be filled with a propellant, a first liquid concentrate filling space to be filled with a first liquid concentrate composition, and a second liquid concentrate filling space to be filled with a second liquid concentrate composition. The double-structure container further includes a discharging mechanism for simultaneously discharging the first liquid concentrate composition and the second liquid concentrate composition from the first liquid concentrate filling space and the second liquid concentrate filling space, respectively.

Figure 2:
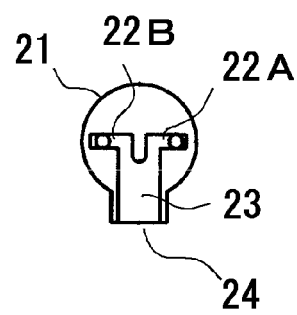
FIG. 2 is a sectional view illustrating a cross section taken along A-A' in FIG. 1.
Figure 3:
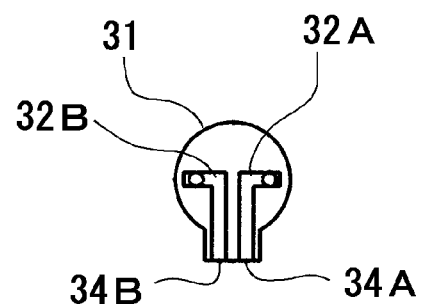
FIG. 3 is an explanatory view illustrating another example structure of a double-structure container used for an aerosol product for forming a gel composition of the present invention.

Specific examples of the double-structure container according to the present invention include the following two containers illustrated in FIG. 1 to FIG. 3.

FIG. 1 is an explanatory view illustrating an example structure of the double-structure container used for the aerosol product for forming a gel composition of the present invention. FIG. 2 is a sectional view illustrating a cross section taken along A-A' in FIG. 1.

This double-structure container 10 includes a pressure resistant container 11 made of metal and provided with an aerosol valve 12. The pressure resistant container 11 is provided thereinside with a first inner bag 15A that is formed of, for example, an aluminum laminated film and that defines a first liquid concentrate filling space to be filled with the first liquid concentrate composition, and a second inner bag 15B that is formed of, for example, an aluminum laminated film and that defines a second liquid concentrate filling space to be filled with the second liquid concentrate composition. In the pressure resistant container 11, a propellant filling space to be filled with the propellant is formed from a gap defined by the pressure resistant container 11, the first inner bag 15A, and the second inner bag 15B. The aerosol valve 12 is provided with a first stem 14A and a second stem 14B each having a stem passage inside. The first stem 14A and the second stem 14B are disposed to be movable up and down inside a first housing 13A and a second housing 13B, respectively. A common actuator 21 is disposed on the upper ends of the first stem 14A and the second stem 14B.

In the example illustrated in the figure, a reference character 16A denotes a first dip tube in communication with the stem passage in the first stem 14A at the lower end of the first housing 13A. The first dip tube 16A extends inside the first inner bag 15A toward the bottom of the pressure resistant container 11. A reference character 16B denotes a second dip tube in communication with the stem passage in the second stem 14B at the lower end of the second housing 13B. The second dip tube 16B extends inside the second inner bag 15B toward the bottom of the pressure resistant container 11.

In FIG. 1, the components located inside the pressure resistant container 11 and the actuator 21 are drawn with broken lines.

The common actuator 21 contains a first actuator passage 22A in communication with the stem passage in the first stem 14A, a second actuator passage 22B in communication with the stem passage in the second stem 14B, and a discharge space 23 in communication with, at its end, the first actuator passage 22A and the second actuator passage 22B and forming, at its another end, a discharge port 24.

The actuator 21 common to the first stem 14A for the first inner bag 15A and the second stem 14B for the second inner bag 15B is provided accordingly so as to form the discharging mechanism for simultaneously discharging the first liquid concentrate composition filled in the first inner bag 15A and the second liquid concentrate composition filled in the second inner bag 15B from the first inner bag 15A and the second inner bag 15B, respectively.

In the double-structure container 10 having such a structure, the first inner bag 15A is filled with the first liquid concentrate composition, the second inner bag 15B is filled with the second liquid concentrate composition, and the propellant filling space is filled with a propellant. The inside of the pressure resistant container 11 is always pressurized with the propellant accordingly. Therefore, when the actuator 21 is actuated (depressed), the pressure of the propellant shrinks the first inner bag 15A and the second inner bag 15B, which causes the first liquid concentrate composition and the second liquid concentrate composition to be discharged simultaneously from the first inner bag 15A and the second inner bag 15B, respectively. As a result, the first liquid concentrate composition and the second liquid concentrate composition are discharged from the discharge port 24 of the actuator 21.

Specifically, while the actuator 21 is not actuated or depressed in the double-structure container 10 filled with the first liquid concentrate composition, the second liquid concentrate composition, and the propellant, the first stem 14A and the second stem 14B are being pushed up to block the stem passage in the first stem 14A and the stem passage in the second stem 14B from the inside of the pressure resistant container 11. While the actuator 21 is actuated or depressed, the first stem 14A and the second stem 14B are pushed down, so that the stem passage in the first stem 14A and the stem passage in the second stem 14B simultaneously communicate with the inside of the pressure resistant container 11. The first liquid concentrate composition in the first inner bag 15A and the second liquid concentrate composition in the second inner bag 15B are discharged simultaneously through the fluid passages formed by the first dip tube 16A and the second dip tube 16B, respectively. The first liquid concentrate composition and the second liquid concentrate composition thus simultaneously discharged reach the discharge space 23 through the stem passage in the first stem 14A and the stem passage in the second stem 14B and through the first actuator passage 22A and the second actuator passage 22B, respectively. The first liquid concentrate composition and the second liquid concentrate composition are discharged from the discharge port 24 without being mixed during passage through the discharge space 23. The first liquid concentrate composition and the second liquid concentrate composition discharged from the discharge port 24 are mixed with, for example, the fingers at an application site to form a gel composition.

FIG. 3 is an explanatory view illustrating another example structure of a double-structure container used for the aerosol product for a gel composition of the present invention. Specifically, FIG. 3 is an explanatory sectional view illustrating the structure of an actuator in accordance with the double-structure container.

This double-structure container has the same structure as that of the double-structure container 10 in accordance with FIG. 1 and FIG. 2 except that the actuator 21 is replaced by an actuator 31 having two discharge ports (specifically, a first discharge port 34A and a second discharge port 34B) and the first liquid concentrate composition and the second liquid concentrate composition are separately discharged from these two discharge ports, respectively.

In other words, the double-structure container in accordance with FIG. 3 includes the actuator 31 and a pressure resistant container having the same structure as that of the pressure resistant container 11 in the double-structure container 10 in accordance with FIG. 1 and FIG. 2.

The actuator 31 is provided with a first actuator passage 32A in communication with, at one end, the stem passage in the first stem and forming a first discharge port 34A at another end, and a second actuator passage 32B in communication with, at one end, the stem passage in the second stem and forming a second discharge port 34B at another end.

The actuator 31 is an actuator common to the first stem and the second stem and is disposed at the upper ends of the first stem and the second stem, like the actuator 21 in the double-structure container 10 in accordance with FIG. 1 and FIG. 2.

While the actuator 31 is actuated or depressed in the double-structure container having such a structure and filled with the first liquid concentrate composition, the second liquid concentrate composition, and the propellant, the first liquid concentrate composition in the first inner bag and the second liquid concentrate composition in the second inner bag are discharged simultaneously. The first liquid concentrate composition is discharged from the first discharge port 34A through the stem passage in the first stem in the aerosol valve and through the first actuator passage 32A, whereas the second liquid concentrate composition is discharged from the second discharge port 34B through the stem passage in the second stem in the aerosol valve and through the second actuator passage 32B. The first liquid concentrate composition and the second liquid concentrate composition discharged from the first discharge port 34A and the second discharge port 34B, respectively, are mixed with, for example, the fingers at an application site or the like to form a gel composition.

In the double-structure container having the structure described above, the discharging mechanism enables simultaneous discharge of the first liquid concentrate composition filled in the first liquid concentrate filling space and the second liquid concentrate composition filled in the second liquid concentrate filling space. The discharging mechanism also allows the amount of the first liquid concentrate composition discharged from the first liquid concentrate filling space and the amount of the second liquid concentrate composition discharged from the second liquid concentrate filling space to be controlled in a suitable quantitative ratio according to, for example, the relationship between the content ratio of the water-soluble alginic acid salt in the first liquid concentrate composition and the content ratio of the dissociative calcium salt in the second liquid concentrate composition.

In the aerosol product for forming a gel composition of the present invention, the mixing ratio of the first liquid concentrate composition discharged from the first liquid concentrate filling space to the second liquid concentrate composition discharged from the second liquid concentrate filling space (the mass of the first liquid concentrate composition: the mass of the second liquid concentrate composition) may preferably be from 0.8:1.2 to 1.2:0.8.

In other words, the amount of the first liquid concentrate composition discharged from the first liquid concentrate filling space and the amount of the second liquid concentrate composition discharged from the second liquid concentrate filling space each may preferably fall within a range of ±20% of the mean of the amounts of the first liquid concentrate composition discharged and the second liquid concentrate composition discharged.

The mixing ratio (the mass of the first liquid concentrate composition: the mass of the second liquid concentrate composition) can be controlled within the above-described range by setting, for example, the viscosity of the first liquid concentrate composition at a temperature of 20° C. to 10 to 125,000 mPa·s, and the viscosity of the second liquid concentrate composition at a temperature of 20° C. to 10 to 125,000 mPa·s.

If the mixing ratio (the mass of the first liquid concentrate composition: the mass of the second liquid concentrate composition) is out of the above-described range, the amount of the first liquid concentrate composition discharged from the first liquid concentrate filling space is significantly different from the amount of the second liquid concentrate composition discharged from the second liquid concentrate filling space. Therefore, a mixed material of the first liquid concentrate composition and the second liquid concentrate composition may fail to have sufficient gel formability.

The aerosol product for forming a gel composition of the present invention described above is produced by filling the first liquid concentrate filling space and the second liquid concentrate filling space in the double-structure container with the first liquid concentrate composition and the second liquid concentrate composition, respectively, and filling the propellant filling space with the propellant.

The aerosol product for forming a gel composition of the present invention has a double-structure container including a discharging mechanism for simultaneously discharging the contents filled in two liquid concentrate filling spaces. One of the two liquid concentrate filling spaces is filled with a first liquid concentrate composition containing water and a water-soluble alginic acid salt, whereas the other is filled with a second liquid concentrate composition containing water and a dissociative calcium salt.

Therefore, the first liquid concentrate composition and the second liquid concentrate composition are mixed to form a gel composition through the ion crosslinking reaction. Since the first liquid concentrate composition and the second liquid concentrate composition can be discharged simultaneously in suitable amounts (specifically, in the same amount) from two liquid concentrate filling spaces, respectively, the first liquid concentrate composition and the second liquid concentrate composition can always be mixed in a constant quantitative ratio, and there is no possibility that the amount of one liquid concentrate composition discharged is much larger than the amount of another liquid concentrate composition discharged. As a result, a desired gel composition can always be obtained easily by simply operating the discharging mechanism, specifically, for example, only depressing the actuator once (one push) to discharge the first liquid concentrate composition and the second liquid concentrate composition.

Moreover, the long-term storage stability can be obtained because neither the first liquid concentrate composition nor the second liquid concentrate composition is exposed to the air outside the container.

Therefore, the aerosol product for forming a gel composition of the present invention can easily and stably form a desired gel composition which has high storage stability.

In the aerosol product for forming a gel composition of the present invention, a non-flammable compressed gas is used as a propellant for the first liquid concentrate composition and the second liquid concentrate composition. The use of the non-flammable compressed gas provides high safety irrespective of the operation environment and eliminates the risk of an explosion accident in discarding the double-structure container.

For the aerosol product for forming a gel composition of the present invention having either an actuator illustrated in FIG. 2 or an actuator illustrated in FIG. 3, the user can enjoy the process for forming the gel composition by mixing the first liquid concentrate composition and the second liquid concentrate composition at an application site or can enjoy changes in the state of a mixture of the first liquid concentrate composition and the second liquid concentrate composition.

The aerosol product for forming a gel composition of the present invention can be used in various applications, such as products for the human body, daily necessaries, and food.

Specifically, the aerosol product can be used as facial masks, medicinal patches, dental impression materials, and the like.

EXAMPLES

Examples of the present invention will be described below, but the present invention is not limited by these.

Example 1

Preparation of First Liquid Concentrate Composition:

A first liquid concentrate composition was prepared by mixing the components described below.

The viscosity of the obtained first liquid concentrate composition at a temperature of 20° C. was measured using a BM-type rotary viscometer (rotor No. 4, 30 rpm, after 1 minute) and found to be 2,000 mPa·s.

Constituents of First Liquid Concentrate Composition:
Purified water: 91.87% by mass
Sodium alginate: 1.50% by mass
Trisodium phosphate: 0.50% by mass
Sodium hyaluronate: 0.10% by mass
"Promois W-42U" (manufactured by Seiwa Kasei Co., Ltd): 0.50% by mass
1,3-Butylene glycol: 5.00% by mass
Phenoxyethanol: 0.30% by mass
Citric acid: 0.02% by mass
Sodium citrate: 0.01% by mass
"Saxifraga Sarmentosa Extract BG" (manufactured by Maruzen Pharmaceuticals Co., Ltd.): 0.10% by mass
"Rosmarinus Officinalis Extract BG-J" (manufactured by Maruzen Pharmaceuticals Co., Ltd.): 0.10% by mass
Total: 100.0% by mass Preparation of Second Liquid Concentrate Composition:

A second liquid concentrate composition was prepared by mixing the components described below.

The viscosity of the obtained second liquid concentrate composition at a temperature of 20° C. was measured using a BM-type rotary viscometer (rotor No. 4, 30 rpm, after 1 minute) and found to be 3,400 mPa·s.

Constituents of Second Liquid Concentrate Composition:
Purified water: 97.70% by mass
Calcium sulfate: 1.00% by mass
Xanthan gum: 1.00% by mass
Phenoxyethanol: 0.30% by mass
Total: 100.0% by mass Production of Aerosol Product:

An aerosol product for forming a gel composition for use as facial masks was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the inner pressure of the double-structure container was 0.7 MPa at 25° C.

The aerosol product for forming a gel composition in Example 1 was applied several times just after production. As a result, it was found that the aerosol product stably formed a desired gel composition.

It was also found that, even after storage in an environment at a temperature of 45° C. for a long period of time or for one month, the aerosol product for forming a gel composition in Example 1 stably formed a gel composition that is similar to that obtained just after production.

REFERENCE SIGNS LIST 10 double-structure container
11 pressure resistant container
12 aerosol valve
13A first housing
13B second housing
14A first stem
14B second stem
15A first inner bag
15B second inner bag
16A first dip tube
16B second dip tube
21 actuator
22A first actuator passage
22B second actuator passage
23 discharge space
24 discharge port
31 actuator
32A first actuator passage
32B second actuator passage
34A first discharge port
34B second discharge port

The invention claimed is:

1. An aerosol product for forming a gel composition, comprising:
   a double-structure container including a propellant filling space and two independent liquid concentrate filling spaces and having a discharging mechanism for simultaneously discharging contents filled in the two liquid concentrate filling spaces, wherein
   the propellant filling space in the double-structure container is filled with a propellant composed of a compressed gas,
   a first liquid concentrate filling space in the double-structure container is filled with a first liquid concentrate composition, and a second liquid concentrate filling space in the double-structure container is filled with a second liquid concentrate composition,
   the first liquid concentrate composition contains water and a water-soluble alginic acid salt,
   the content ratio of water in the first liquid concentrate is 91.87% to 99.5% by mass per 100% by mass of the first liquid concentrate composition,
   the content ratio of the water-soluble alginic acid salt in the first liquid concentrate composition is not less than 0.5% by mass per 100% by mass of the first liquid concentrate composition,
   the second liquid concentrate composition contains water and a dissociative calcium salt,
   the content ratio of the dissociative calcium salt in the second liquid concentrate composition is 0.3% to 20% by mass per 100% by mass of the second liquid concentrate composition, and
   the first liquid concentrate composition discharged from the first liquid concentrate filling space and the second liquid concentrate composition discharged from the second liquid concentrate filling space are mixed to form a gel composition.

2. The aerosol product for forming a gel composition according to claim 1, wherein a mixing ratio of the first liquid concentrate composition to the second liquid concentrate composition (a mass of the first liquid concentrate composition: a mass of the second liquid concentrate composition) discharged from the discharging mechanism is from 0.8:1.2 to 1.2:0.8.

3. The aerosol product for forming a gel composition according to claim 1, wherein the first liquid concentrate composition has a viscosity of 10 to 125,000 mPa·s at a temperature of 20° C., and the second liquid concentrate composition has a viscosity of 10 to 125,000 mPa·s at a temperature of 20° C.

4. The aerosol product for forming a gel composition according to claim 1, wherein the water-soluble alginic acid salt contained in the first liquid concentrate composition is at least one selected from the group consisting of sodium alginate, potassium alginate, and ammonium alginate.

5. The aerosol product for forming a gel composition according to claim 1, wherein the container contains a valve, the valve comprising:
   a first housing and a second housing; and
   a first stem and a second stem,
   wherein the first stem and the second stem are disposed to be movable up and down inside the first housing and the second housing, respectively, and
   the first liquid concentrate filing space and the second liquid concentrate filing space are connected to the first housing and the second housing, respectively.

6. The aerosol product for forming a gel composition according to claim 5, wherein the first housing and the second housing extend from the valve into the container.

7. The aerosol product for forming a gel composition according to claim 1, wherein the liquid concentrate filling spaces are two separate bags.

8. The aerosol product for forming a gel composition according to claim 7, wherein each of the bags is formed from an aluminum laminated film.

9. The aerosol product for forming a gel composition according to claim 1, wherein the propellant filling space in the double-structure container is filled with the propellant so as to have an inner pressure within a range of 0.3 to 1.2 MPa at 25° C.

10. The aerosol product for forming a gel composition according to claim 1, wherein the content ratio of water in the second liquid concentrate composition is 80% to 99.7% by mass per 100% by mass of the second liquid concentrate composition.

* * * * *